United States Patent
Robins-Browne et al.

(10) Patent No.: US 9,402,902 B2
(45) Date of Patent: *Aug. 2, 2016

(54) COMPOSITION AND METHOD FOR THE TREATMENT AND PREVENTION OF ENTERIC BACTERIAL INFECTIONS

(71) Applicant: Immuron Limited, Southbank (AU)

(72) Inventors: Roy Michael Robins-Browne, Templestowe (AU); Grant Thomas Rawlin, Kilmore East (AU); Gottfried Lichti, Essendon (AU)

(73) Assignee: Immuron Limited, Southbank, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/138,834

(22) Filed: Dec. 23, 2013

(65) Prior Publication Data

US 2014/0112938 A1    Apr. 24, 2014

Related U.S. Application Data

(62) Division of application No. 10/548,156, filed as application No. PCT/AU2004/000277 on Mar. 4, 2004, now Pat. No. 8,637,025.

(30) Foreign Application Priority Data

Mar. 4, 2003 (AU) ................ 2003901008

(51) Int. Cl.
| | |
|---|---|
| *A61K 39/40* | (2006.01) |
| *A61B 5/0205* | (2006.01) |
| *A61B 5/00* | (2006.01) |
| *A61B 5/021* | (2006.01) |
| *A61B 5/024* | (2006.01) |
| *A61B 17/00* | (2006.01) |

(52) U.S. Cl.
CPC ............... *A61K 39/40* (2013.01); *A61B 5/0205* (2013.01); *A61B 5/4821* (2013.01); *A61B 5/7264* (2013.01); *A61B 5/021* (2013.01); *A61B 5/024* (2013.01); *A61B 5/7267* (2013.01); *A61B 2017/00022* (2013.01)

(58) Field of Classification Search
None
See application file for complete search history.

(56) References Cited

U.S. PATENT DOCUMENTS

| | | | |
|---|---|---|---|
| 4,298,597 A | 11/1981 | Acres et al. | |
| 4,971,794 A | 11/1990 | Linggood et al. | |

FOREIGN PATENT DOCUMENTS

| | | |
|---|---|---|
| EP | 0074240 B1 | 3/1983 |
| GB | 1560934 A | 2/1980 |
| WO | 8501659 A1 | 4/1985 |
| WO | 95/08562 A | 3/1995 |
| WO | 03/080082 A1 | 10/2003 |

OTHER PUBLICATIONS

Tacket et al. (N. Engl. J. Med. 318:1240-1243, 1988).*
Konadu et al., "Preparation, Characterization, and Immunological Properties in Mice of *Escherichia coli* O157 O-Specific Polysaccharide-Protein Conjugate Vaccines," Infect. Immun. 62:5048-5054 (1994).
Voet et al. "Other Pathways of Carbohydrate Metabolism," Biochemistry. 2nd ed. New York: John Wiley & Sons, Inc. 1995:599-625.
Konadu et al., "Phase 1 and Phase 2 Studies of *Salmonella enterica* Serovar Paratyphi A O-Specific Polysaccharide-Tetanus Toxoid Conjugates in Adults, Teenagers, and 2- to 4-Year-Old Children in Vietnam," Infect. Immun. 68 (3):1529-1534 (2000).
Bennet-Guerrero et al., "Preparation and Preclinical Evaluation of a Novel Liposomal Complete-Core Lipopolysaccharide Vaccine," Infect. Immun. 68(11):6202-6208 (2000).
Robbins et al., "Hypothesis for Vaccine Development: Protective Immunity to Enteric Diseases Caused by Nontyphoidal Salmonellae and Shigellae May be Conferred by Serum IgG Antibodies to the O-Specific Polysaccharide of their Lipopolysaccharides," Clin. Infect. Dis. 15(2):346-361 (1992).
Conlan et al., "Mice Vaccinated with the O-Antigen of Fracisella tularensis LVS Lipopolysaccharide Conjugated to Bovine Serum Albumin Develop Varying Degrees of Protective Immunity Against Systemic or Aerosol Challenge with Virulent Type A and Type B Strains of the Pathogen," Vaccine 20:3465-3471 (2002).
Hormaeche et al., "Protection Against Oral Challenge Three Months After I.V. Immunization of BALB/c Mice with Live Aro *Salmonella typhimurium* and *Salmonella enteritidis* Vaccines is Serotype (Species)-Depndent and Only Partially Determined by the Main LPS O Anitgen," Vaccine 14(4):251-259 (1996).

* cited by examiner

*Primary Examiner* — Brian J Gangle
(74) *Attorney, Agent, or Firm* — LeClairRyan, a Professional Corporation

(57) ABSTRACT

The present invention provides a method of treatment or prophylaxis of enteric disease caused by Gram negative bacteria. The method includes the step of administering a vaccine or a hyperimmune material raised against said vaccine to an individual. The vaccine comprises one or more cell wall antigens reactive in a manner characteristic of O group serotypes, or reactive in a manner characteristic of lipopolysaccharide associated antigens, and at least some of said antigens are separated from bacterial cell walls or wall fragments. The invention also provides composition containing hyperimmune material as well as uses of the composition and vaccine.

11 Claims, 1 Drawing Sheet

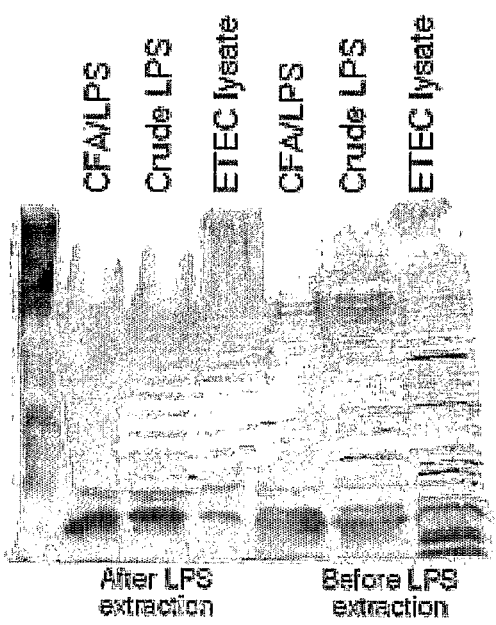

COMPOSITION AND METHOD FOR THE TREATMENT AND PREVENTION OF ENTERIC BACTERIAL INFECTIONS

This application is a divisional of U.S. patent application Ser. No. 10/548,156, filed Mar. 4, 2004, which is a national stage application under 35 U.S.C. §371 from PCT Application No. PCT/AU2004/000277, filed Mar. 4, 2004, which claims the benefit of Australia Patent Application Serial No. 2003901008, filed Mar. 4, 2003, all of which are hereby incorporated by reference in their entirety.

FIELD OF THE INVENTION

The present invention relates to treatment and prophylaxis of gastrointestinal disorders, to vaccines comprising antigens of gastrointestinal pathogens and to immune materials derived from blood, milk and eggs produced when animals including cattle and poultry are injected with the said vaccines and methods for their preparation. In particular the invention relates to compounds and compositions for treatment or prophylaxis of gastrointestinal disorders, such as diarrhoea, caused by Gram negative bacteria such as enterotoxigenic E. coli bacteria and to a method of treatment or prophylaxis of diarrhoea.

BACKGROUND OF THE INVENTION

The present invention may be used in the treatment and prophylaxis of gastrointestinal diseases caused by a range of organisms including *E. coli, Salmonella, Campylobacter, Helicobacter, Vibrio, Shigella, Yersinia* and *Aeromonas* bacteria. For the purposes of exposition, however, the invention will be explained in its application to enterotoxigenic *E. coli* (ETEC) in humans. It will be understood however that the broadest part of the invention is not limited by this exemplary application.

Diarrhoea caused by enterotoxigenic *E. coli* (ETEC) causes significant discomfort in adults and can lead to death through dehydration of young and older people. A significant fraction of the diarrhoea suffered by travellers to destinations such as Mexico, Africa and South-East Asia is caused by ETEC.

One treatment currently used for travellers' diarrhoea is prophylactic antibiotic therapy, for example with Amoxycillin. However antibiotic resistance has reduced the effectiveness of antibiotic therapy and side-effects such as constipation or diarrhoea are common.

Symptomatic therapy is used for vomiting and diarrhoea, for example with loperamide hydrochloride, atropine sulphate and diphenoxylate hydrochloride. However the inappropriate use of Loperamide and Atropine leads to severe constipation and the inappropriate use of diphenoxylate may lead to dependence. These agents are also unsuitable for administration to children.

A further treatment includes fluid replacement therapy using isotonic drinks. However fluid replacement therapy is merely palliative, and does not decrease clinical diarrhoea Furthermore symptomatic relief and fluid therapy will treat the symptoms but will not remove the cause.

Milk and egg products have been shown to have potential therapeutic and preventative roles in the relief of symptoms of gastrointestinal disorders Peterson and Campbell in U.S. Pat. No. 3,376,198 teach the immunisation of milk-producing ungulates to produce antibodies or "protective principles" against bacteria and viruses.

Carlander et al in BioDrugs 2002; 16(6):433-7 teach the use of antibodies derived from egg yolk to decrease *Pasteurella* bacteria in the opening of the gastrointestinal tract (the mouth).

Shimamoto et al in Hepatogastroenterology 2002 49(45): 709-714 teaches the use of specific antibodies against *Helicobacter pylori* raised in eggs to decrease the number of *H. pylori* bacteria in the stomach of patients.

Linggood et al in U.S. Pat. No. 4,971,794 teach the use of hyperimmune bovine colostrum as a source of antibodies to *E. coli*. The cows were vaccinated using preparations of pili from a mixture of strains. The patent teaches that the vaccine must comprise antigens of a plurality of strains of *E. coli* expressing Type 1 pili, CFA 1 pili, CFA 2 pili and K88 pili. K88 is associated with porcine ETEC.

Hastings in U.S. Pat. No. 5,017,372 teaches the use of hyperimmune colostrum from ungulates as a source of antibodies to *E. coli*. The ungulate vaccine was made using the following method: Various *E. coli* bacteria were grown under conditions so that CFA 1 or CFA 2 or both were produced. The bacteria were then lysed by ultrasound to release these antigens and heat labile toxins.

Freedman et al in The Journal of Infectious Diseases 1998, 177:662-7 teaches the use of hyperimmune colostrum as a source of antibodies against *E. coli*. A vaccine was made by growing bacteria strains in a broth designed to optimise CFA expression, then purifying the CFA using precipitation followed by size-exclusion or ion exchange chromatography.

Tackett et al in The New England Journal of Medicine May 12, 1988 pp 1240-1243 describe the pooling of multiple inactivated (formaldehyde or glutaraldehyde treated) bacterial whole cell suspension in a vaccine administered to cattle. The whole-cell suspensions comprise *E. coli* of O serogroups: O6, O8, O15, O20, O25, O27, O63, O78, O114, O115, O128, O148, O153 and O159 as well as heat-labile enterotoxins, cholera toxin, CFA 1 and *E. coli* surface antigen 3. O antigens of *E. coli* such as O6, O8, O15, O20, O25, O27, O63, O78, O114, O115, O128, O148, O153 and O159 are heat stable antigens located on the bacterial cell wall and not on protruding structures such as pili (fimbriae) or flagella. These O antigens are composed of polysaccharide moieties linked to a core lipooligosaccharide complex common to the wall material of most Gram negative bacteria. Because of the close association between the O antigens and the cell wall, O antigen based vaccines have been made from cell walls or whole inactivated bacteria. The lipopolysaccharide endotoxins are a normal part of the outer cell wall of the bacteria and their toxic regions are embedded in the cell wall (see "Endotoxins in Health and Disease", 1999 Chapter 12 and other chapters). A further reason for the fact that normal veterinary practice uses whole cell bacterial antigens rather than individual O antigen moieties is that O antigens are endotoxins—the use of high concentrations of endotoxins in pregnant cattle is considered problematic in prior art in terms of animal welfare and productivity.

The use of milk and egg products in the prior art for the prevention of symptoms of gastrointestinal disorders is associated with a number of problems.

Cholera toxin (see Tackett et al., 1988) are likely to be difficult to register because of their high toxicity. Further, heat labile toxins, although highly immunogenic are not likely to be protective.

The extent of protection obtained from antibodies produced as above is unsatisfactory. One of the attendant problems is that large quantities of immune concentrate are needed to produce a satisfactory prophylactic outcome. When whole cell antigens are used, an enormous variety of antibody responses arise and assays for antibody titre are difficult to interpret. A key issue is whether a particular detected antibody is protective or not. Whole bacterial cells have many antigens that are unlikely to be related to protection. In addition, vaccines comprising Gram negative bacteria are more likely to produce adverse vaccine reactions and therefore present regulatory problems due to adverse animal ethics reports and therapeutic goods adverse reaction reports. Adverse vaccine reactions are likely to stop dairy farmers from participating in any production venture for milk antibodies.

The discussion of the background to the invention herein is included to explain the context of the invention. This is not to be taken as an admission that any of the material referred to was published, known or part of the common general knowledge in any country.

SUMMARY OF THE INVENTION

We have made the surprising discovery that enhanced treatment or prophylaxis of enteric disease caused by Gram negative bacteria in animals and humans can be achieved by administering a vaccine or by administering hyperimmune material raised against said vaccine, wherein the vaccine is characterised in that it comprises one or more cell wall antigens reactive in a manner characteristic of O group serotypes or reactive in a manner characteristic of lipopolysaccharide-associated antigens, at least some of said antigens being separated from bacterial cell walls or wall fragments.

Accordingly in one aspect the invention provides a method of treatment or prophylaxis of enteric disease caused by Gram negative bacteria, the method including the step of administering a vaccine or a hyperimmune material raised against said vaccine to an individual, wherein the vaccine comprises one or more cell wall antigens reactive in a manner characteristic of O group serotypes, or reactive in a manner characteristic of lipopolysaccharide associated antigens, at least some of said antigens being separated from bacterial cell walls or wall fragments.

In another aspect the invention provides a composition for use in the treatment or prophylaxis of enteric disease caused by Gram negative bacteria, the composition comprising hyperimmune material prepared by immunizing a host animal with a vaccine comprising one or more cell wall antigens reactive in a manner characteristic of O group serotypes, or reactive in a manner characteristic of lipopolysaccharide associated antigens, at least some of said antigens being separated from bacterial cell walls or wall fragments.

In yet another aspect the invention provides a method of preparing hyperimmune material for treatment or prophylaxis of gastrointestinal dysfunction caused by enterotoxigenic Gram negative bacteria such as ETEC, said hyperimmune materials being raised against a vaccine comprising one or more cell wall antigens reactive in a manner characteristic of O group serotypes, or reactive in a manner characteristic of lipopolysaccharide associated antigens, at least some of said antigens being separated from bacterial cell walls or wall fragments.

In a further aspect the invention provides the use of cell wall antigens in the manufacture of hyperimmune material for treatment or prophylaxis of gastrointestinal disease caused by Gram negative bacteria such as *E. coli* (ETEC) wherein the cell wall antigens are reactive in a manner characteristic of O group serotypes, or reactive in a manner characteristic of lipopolysaccharide associated antigens, at least some of said antigens being separated from bacterial cell walls or wall fragments.

In yet another aspect the invention provides a process for the preparation of immunoglobulins for treatment or prophylaxis of gastrointestinal disease in animals comprising immunising a host animal with a vaccine comprising one or more cell wall antigens reactive in a manner characteristic of O group serotypes, or reactive in a manner characteristic of lipopolysaccharide associated antigens, at least some of said antigens being separated from bacterial cell walls or wall fragments to thereby induce the host animal to produce hyperimmune material comprising the immunoglobulins.

The hyperimmune material that is produced according to the methods of the invention may be hyperimmune colostrum or hyperimmune colostrum extract or hyperimmune egg yolk or hyperimmune egg yolk extract.

At least some of the cell wall antigens are considered to be separated from intact bacterial cell walls or cell wall fragments if, after centrifugation to remove whole cells and substantial cell fragments, at least 10% of said antigens can be detected in the supernatant liquor. This centrifugation should be performed under conditions where a) said antigens do not form micelles or other aggregated structures and b) cell wall integrity is not compromised. Preferably at least 20% of said antigens can be detected in the supernatant liquor, more preferably at least 30%. Preferably said antigens are substantially separated from intact bacterial cell walls.

Another procedure that can be used to determine if cell wall antigens are separated or disassociated from intact bacterial cell walls or cell wall fragments is as follows: 1) Perform an assay on an aqueous liquor comprising O antigens and Gram negative bacterial cell walls or cell wall fragments to determine total O antigen content per ml using vigorous conditions which will degrade cell wall structure and release O antigens; 2) Establish which specific concentration of Gram negative cells, grown in culture, have an O antigen content equivalent to the O antigen content determined in step 1; 3) Measure the cell wall content (quantity) per ml of the cell culture identified in step 2. This cell wall content will naturally contain the level of O antigen measured in step 1. 4) Compare the cell wall content in step 3 with the content of the original liquor. If equivalent, it may be inferred that all O antigens in the original liquor have their usual association with the cell wall. However, if the cell wall content of the original liquor is less than the cell wall content in step 3 then the original liquor contains O antigens in excess of the expected O antigen content of cell walls and therefore some O antigen is dissociated from the cell walls or wall fragments. If the weight of Gram negative cell wall material (per ml) in Step 3 is W, then it is preferred that the weight per ml of Gram negative wall material in the original liquor is less than 0.8 W, preferably less than 0.3 W, more preferably less than 0.1 W.

The quantity of lipopolysaccharide-associated antigen (O antigen) present in an aqueous liquor can be determined using methods known to the art such as heating, proteinase K digestion and further heating in the presence of phenol (see example 11). Other assays for lipopolysaccharide-associated antigens have been described by Lyngby et al. One convenient method of standardising lipopolysaccharide-associated antigens is to compare with a cell culture having a specified number of Gram negative organisms per ml, or a specified quantity of Gram negative wall material per ml. It may be advantageous to compare with cell cultures having $10^4$, $10^6$ or $10^8$ organisms per ml, or higher.

The quantity of Gram negative cell wall material (intact walls and fragments) present in an aqueous liquor can be determined using assays for specific cell wall markers known in the art. For example peptidoglycans are associated with the cell walls of Gram negative bacteria, and methods of analysing peptidoglycans have been described by Li et al.

DESCRIPTION OF THE FIGURES

FIG. 1 shows a silver-stained SDS-PAGE gel from the analysis of LPS from a liquor preparation. Shown on the SDS-PAGE gel are samples before and after phenolic pretreatment. After the treatment this gel shows a typical LPS ladder. Also shown in left lane as a control is a boiled bacterial lysate.

DETAILED DESCRIPTION OF THE INVENTION

In the following detailed description of the invention we refer predominantly to the production and use of hyperimmune colostrum and hyperimmune colostrums extract that is obtained from suitably immunized cows. However, the scope of the invention should not be taken to be restricted thereto and it is envisaged that the methods described can also be used in the production of hyperimmune egg yolk and hyperimmune egg yolk extract.

The preparation of hyperimmune colostrum will generally comprise immunising a host animal, typically an ungulate animal, with a vaccine comprising the cell wall antigens of O group serotype at least some of which are separated from intact cell walls. The vaccine is used to induce production in the host animal of immunoglobulins which are recovered in the milk of the host.

The hyperimmune colostrum may be used in treatment or prophylaxis of gastrointestinal dysfunction in animals including humans and non-human animals. The colostrum is particularly useful in treatment or prophylaxis in humans including adult and infant humans. The colostrum may however be used in treatment of non-human animals including piglets.

The hyperimmune colostrum from the host animal immunized with the cell wall antigens vaccine may be administered directly in the form of milk. Alternatively the hyperimmune colostrum milk may be treated by methods known in the art to enrich or isolate the immunoglobulins. Thus the product may be whole milk, skim milk or whey protein.

The products derived from the hyperimmune colostrum may be prepared in preparations such as food additives, aqueous solutions, oily preparations, emulsions, gels, etc., and these preparations may be administered orally, topically, rectally, nasally, bucally, or vaginally. The preparations may be administered in dosage formulations containing conventional non-toxic acceptable carriers and may also include one or more acceptable additives, including acceptable salts, polymers, solvents, buffers, excipients, bulking agents, diluents, excipients, suspending agents, lubricating agents, adjuvants, vehicles, delivery systems, emulsifiers, disintegrants, absorbents, preservatives, surfactants, colorants, flavorants or sweeteners. A preferred dosage form of the present invention is a powder for incorporation into beverages, pills, syrup, capsules, tablets, granules, beads, chewable lozenges or food additives, using techniques known in the art.

In the case where the composition is administered as a tablet, the tablet may be made by compressing or moulding the active ingredient, with one or more accessory ingredients optionally included. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made in a suitable machine, by moulding together a mixture of the powdered active ingredient and a suitable carrier, moistened with an inert liquid diluent.

The O antigens can be separated from the bacterial cell walls by application of an effective amount of shear, homogenisation or heat or by effective combinations thereof. The preferred conditions used to effect the separation can be established by carrying out the following test: Centrifuge the whole cell suspension which has been treated to effect the separation and remove the whole cells and substantial cell fragments. Collect the resultant cell-free liquor and run on a gel according to the following protocol:

A) Analysis of LPS from Cell Free Liquors

Add an equal volume of standard phenol solution to a liquor sample obtained as described previously, vortex and incubate in a waterbath at 65° C. for 15 mins vortexing every 5 mins to denature protein in the liquor.

Centrifuge for 10 mins at 4° C. and recover aqueous phase to a fresh tube.

Add 1 volume of 3× Laemmli buffer to 2 volumes of sample and separate on a 15% SDS-PAGE gel.

B) Silver Staining of LPS

The following procedure is used to preferentially stain LPS (Hitchcock and Brown, 1983):

(i) overnight fixation in 200 mL of 25% (vol/vol) isopropanol in 7% (vol/vol) acetic acid (ii) 5 minute oxidation in 150 mL of distilled water with 1.05 g of periodic acid and 4 mL of 25% (vol/vol) isopropanol in 7% (vol/vol) acetic acid (solution made up just before use)

(iii) eight 30 minute washes with 200 mL of distilled water each time (iv) 10 minute silver-staining in a solution consisting of 0.1 M NaOH (28 mL), concentrated (29.4%) ammonium hydroxide, 20% (w/vol) silver nitrate (5 mL), and distilled water (115 mL) (make solution just before use and stir constantly while making)

(v) four 10 minute washes with 200 mL of distilled water each time (vi) 5-10 minutes developing in 250 mL of developer solution (citric acid [50 mg], 37% formaldehyde [0.5 mL], distilled water [amount sufficient to make 1 liter of solution] made up just before use at an optimal temperature of 26° C. to help preferential staining of LPS (vii) 1 hour in stop solution (200 mL of distilled water plus 10 mL of 7% [vol/vol]acetic acid (viii) store gel in 5% glycerol and dry between cellulose sheets In a particularly preferred embodiment of the invention the O antigens are separated from the bacterial cell walls by agitating the liquor, for instance by using a homogeniser, typically a homogeniser comprising a rotor and a stator.

Preferably the ratio of the peripheral speed of the rotor (in meters per second) to the rotor-stator gap (in millimeters) is in a range of 0.2 to 20, preferably 0.4 to 12, more preferably 0.8 to 6 and most preferably 1 to 4. Other homogenisers may be used in which the region of maximum shear has a shear value similar to the shear value in the above rotor-stator gaps. In one preference the O antigens are separated from the cell wall by heat treatment in the range 40 to 80° C., preferably 50 to 70° C. The duration of the treatment is preferably 10 to 200 minutes, more preferably 30 to 60 minutes.

It is preferred that the vaccine further comprises the pilus or pilus-like antigens CFA-1 or CFA-2 or other CFAs or putative CFAs or combinations thereof, at least some of said antigens being separated from intact bacterial cell walls. These antigens may be associated with pili which have broken off from the cell wall. Methods of preparing said separated antigens or pili have been described in the art, for example Linggood in U.S. Pat. No. 4,971,794.

It is preferred the bacteria from which each type of O antigen is isolated are grown in separate bacterial culture systems, and after separation of the O antigen from the bacteria, the component antigens are added together to form a component of the vaccine.

It is preferred that the serotype O antigens in the vaccine are chosen from the set: O6, O8, O15, O25, O27, O63, O78, O114, O115, O128, O148, O153, O159, and other serotype O antigens associated with enterotoxigenic *E. coli*. Most preferably the serotype O antigens in the vaccine comprise O78.

The liquor containing the separated O antigen may contain extraneous material. In one preference the liquor is further purified by ammonium sulphate precipitation of extraneous proteins, which involves gradually increasing the ammonium sulphate concentration from 0 to 20%, and centrifuging the extraneous material.

In one preference the separated O antigen is further concentrated. In one preference to the above liquor at 20% ammonium sulphate, further ammonium sulphate is added to a final concentration of 40% and centrifuged to provide O antigens in the precipitate. The ammonium sulphate can be removed by resuspension and dialysis, for example through a membrane having a cut-off size in the range 1,500-10,000 molecular weight units (Daltons).

The dialysed material is preferably constituted in the range of 0.1 to 10 mg/ml of protein preferably 0.5 to 3 mg/ml of protein, and added to a vaccine adjuvant such as MONTANIDE (sold by Seppic, Paris, France), Aluminium Hydroxide (available from Sigma Chemical Company, St Louis, Mo., USA) or QuilA (an ISCOM consisting of antigen modified saponin/cholesterol micelles and described in U.S. Pat. No. 6,383,498) or other vaccine adjuvants known to the art.

In one preferred form of the invention the adjuvant used to prepare a vaccine emulsion is "MONTANIDE ISA 206", an NRA approved veterinary adjuvant made by Seppic and supplied by Tall Bennett in Australia. MONTANIDE ISA 206 is an immunostimulant composition containing esters of octadecenoic acid and anhydromannitol in an oily solution. It has been developed for the manufacture of mixed oil vaccines and is toxicologically controlled and of high purity. This adjuvant allows the preparation of a mixed type "water in oil in water" (w/o/w) immunogen/adjuvant emulsion, which is effective, well tolerated, very fluid and easy to inject. This type of formulation produces a rapid immune response from the immediately available antigens present in the aqueous phase and a durable immune response from the antigen confined in the oily phase.

In one preference one volume of constituted dialysed material is added to 0.3 to 3 volumes of vaccine adjuvant, preferably 0.7 to 1.5 volumes of vaccine adjuvant. Many methods of analysing for protein are known to the art, for example the Lowrey protein assay (J. Biol Chem 1951, 193: 265-275).

The vaccination regimen leading to the production of hyperimmune colostrum preferably involves the injection of an animal with 0.3 to 15 mL of vaccine on 2 to 8 occasions prior to parturition. The time period between successive vaccinations is 1 to 4 weeks, more preferably 2 to 3 weeks. Colostrum is derived from mammals, preferably ungulates, more preferably dairy cows. Methods for production and processing of colostrum are provided in U.S. Pat. No. 5,780, 028 the contents of which are incorporated by reference.

The processed hyperimmune colostrum can be formulated as a tablet or as a powder within a capsule or as an additive to a drink mix as described in U.S. Pat. No. 5,780,028.

Preferably the formulation comprising hyperimmune colostrum further comprises a food-grade antimicrobial moiety, such as citrus extracts and iodine based antiseptics. In one preference the antimicrobial moiety is the grapefruit seed extract of the chemical family diphenol hydroxybenzene sold under the product name CITRICIDAL by NutriBiotics of Ripton, Vt., USA.

A preferred hyperimmune colostrum for an oral dose formulation comprises antibodies against a plurality of antigens. Said preferred hyperimmune colostrum is made by separating said antigens into two or more vaccine lots and vaccinating two or more herds of cattle with individual lots, and blending the colostrum from the herds.

In one preference the vaccine will comprise *E. coli* O antigens chosen from the set consisting of O6, O8, O9, O15, O20, O25, O27, O29, O30, O63, O64, O78, O88, O105, O114, O115, O126, O127, O128, O148, O153, O159.

Preferably one vaccine lot will comprise *E. coli* O78 antigen and CFA1 pilus antigen, and the other vaccine lot will comprise antigens chosen from the set consisting of O6, O8, O15, O25, O27, O63, O78, O114, O115, O128, O148, O153, O159 serotype O antigens and CFA 2 pilus antigen.

In one preference the serotype O antigens are chosen from the set O6, O8, O78, O128.

While in its broadest aspect the invention may be applied in this treatment or prophylaxis of gastrointestinal disease caused by a range of organisms it is particularly suited to treatment of gastrointestinal infections of enterotoxigenic *E. coli* and particularly in treatment or prophylaxis of traveller's diarrhoea. Accordingly in a particularly preferred embodiment the invention relates to a method or use as defined above wherein the Gram negative bacteria is *E. coli*. In the most preferred embodiment the method is used in prophylaxis or treatment of diarrhoea.

The invention will now be described with reference to the following examples. It is to be understood that the examples are provided by way of illustration of embodiments of the invention and that they are in no way limiting to the scope of the invention.

Example 1

Manufacture of a Single Strain *E. coli* Vaccine

This example describes the preparation of a vaccine according to the invention in which the wall antigen is O78 and the pilus antigen is CFA1. The procedure is as follows.
Day 0
(Step A) Strain Rejuvenation The strain to be rejuvenated is *E. coli* H10407 (Taurchek et al, PNAS USA 2003, 99:7066-7071). Take 2 CFA plates (Evans et al, Infect Immun 1977; 18:330-337) from the media refrigerator and place them in the biological safety cabinet. Remove the vial containing *E. coli* H 10407 from the liquid nitrogen tank and place it in the biological safety cabinet. Open the vial and use a sterile loop to remove a small quantity of frozen material. Streak this material onto CFA plates. Place the "rejuvenation plates" in the 37° C. incubator overnight under aerobic conditions.
Day 1
(Step B) Inoculation of "Starter Suspension"

Examine each "rejuvenation plate" for pure growth. If pure growth is present proceed.

Working in the biological safety cabinet, remove several colonies from one "rejuvenation plate" with a sterile loop and inoculate a McCartney bottle containing 20 mL of phosphate buffered saline (PBS) pH 7.2. Use McCartney bottles and PBS that have been sterilised by autoclaving.

(Step C) Inoculation of "Vaccine Plates"

Inoculate 50 µL of "starter suspension" onto each of multiple CFA plates (microbiological nutrient plates formulated to enable production of CFA).

CFA plates are prepared using 1% casamino acids (BD Difco) and 0.15% yeast extract (Oxoid) in 2% agar containing 0.005% $MgSO_4$ (anhydrous) and 0.0005% $MnCl_2$ (tetrahydrate), as described in media preparation (Evans et al, Infect Immun 1977; 18:330-337). Place the "vaccine plates" in the 37° C. incubator for 18-24 hours under aerobic conditions.

Day 2

(Step D) Haemagglutination Test on "Vaccine Plates" to Test for Pilus Production Carry out the Haemagglutination test (Evans et al, Infect Immun 1977; 18:330-337). Test one "vaccine plate" for each strain to be used in the batch. If positive proceed.

(Step E) Washing of "Vaccine Plates"

Remove the "vaccine plates" from the incubator. Check each one for contamination and reject any affected plates.

Working in the biological safety cabinet, use 1.5-2.0 mL of sterile 0.1 M sodium phosphate buffer (pH 7.2) to wash the bacterial growth from the surfaces of the "vaccine plates" into a sterile Schott bottle. Pre-cool the buffer on ice before use. Add sodium azide to a final concentration of 0.05% to the "vaccine washings".

Keep the "vaccine washings" on ice for at least 30 minutes before commencing homogenisation.

(Step F) Enumeration of "Vaccine Washings"

Carry out enumeration of the "vaccine washings". Ensure that the material has been thoroughly agitated to disperse all clumps and that the dilutions chosen are appropriate to the degree of concentration of bacterial cells in the washings for the batch being manufactured.

(Step G) Purity Sampling

Assemble sufficient materials for purity testing each "vaccine washing" (ie; 3 HBA Plates, 3 TSA Plates and 3 MAC plates).

Working in the biological safety cabinet, streak out each "vaccine washing" onto 3 HBA, 3 TSA and 3 MAC plates, plating for single colonies. Place the plates in the 37° C. incubator under aerobic conditions.

Day 3

(Step H) First Reading of the "Purity Test Plates"

Carry out the first reading on the "purity test plates". If the plates contain only colonies of E. coli proceed.

(Step I) Homogenisation of "Vaccine Washing"

Homogenise the "vaccine washing" in the homogeniser for a total of 15 minutes at one minute intervals, with one minute of cooling in an ice-bath between each interval. Centrifuge the "homogenised vaccine washing" in the high speed centrifuge at 12,000×g for 20 minutes at 4° C. Keep the supernatants (HVW super 1) and store at 4° C. for 1-3 days.

Day 4

(Step J) Second Reading of the "Purity Test Plates"

Carry out the second check on the purity test plates. If the plates contain only pure colonies of E. coli proceed.

Day 6

(Step K) Separation of LPS Fraction

Centrifuge the "HVW super 1" in the high speed centrifuge at 12,000×g for 20 minutes at 4° C. Keep the supernatant (HVW super 2).

Add sterile saturated ammonium sulphate to the "HVW super 2" slowly over 1 hour until 20% saturation is reached. Stir the "HVW super 2" on a magnetic stirrer while adding the saturated ammonium sulphate. At the end of the hour allow the material to equilibrate for 30 minutes.

Centrifuge the "HVW super 2" in the high speed centrifuge at 12,000×g for 20 minutes. Keep the supernatant (HVW super 3).

Add sterile saturated ammonium sulphate to the "HVW super 3" slowly over 1 hour until 40% saturation is reached. Stir the "HVW super 3" on a magnetic stirrer while adding the saturated ammonium sulphate. At the end of the hour allow the material to equilibrate for 30 minutes.

Centrifuge the "HVW super 3" in the high speed centrifuge at 12,000×g for 20 minutes. Keep the pellet (LPS fraction). Resuspend the "LPS fraction" in cold 0.05M sodium phosphate buffer pH 7.2 at a ratio of 10 mL buffer for each 250 CFA plates that were used to produce the "vaccine washing" from which the "LPS fraction" was originally derived.

(Step L) Dialysis of "LPS Fractions"

Dialyse the "LPS" fraction, using a 3,500 MW cut-off membrane, for 24-48 hours at 4° C. against 250-1,000 volumes of cold 0.05M sodium phosphate buffer pH 7.2. Change the buffer every 2-8 hours during dialysis. When complete, keep the "LPS dialysate" on ice until ready to assay the protein content.

Day 7

(Step M) Assaying Protein Content of "LPS Dialysate"

Use the Lowry protein assay to measure the protein content of each "LPS dialysate". On the basis of the results dilute each "LPS dialysate" so that it contains 1 mg/mL of protein in 0.05M sodium phosphate buffer pH 7.2, and store in a sterile Schott bottle.

(Step N) Inactivation of Vaccine

Add formaldehyde to each "LPS dialysate" so that the final concentration of formalin is 0.3%. Store the "formalinised LPS dialysate" at 4° C. for 3 days.

Day 10

(Step O) Sterility Checking Part 1

Carry out a basic sterility check on each "formalinised LPS dialysate" by inoculating 0.5 mL of each into 3 TSB tube broths. Place the "sterility check tubes" in the 37° C. incubator under aerobic conditions.

Day 14

(Step P) Sterility Checking Part 2

Check the "sterility check tubes" for absence of growth. If pure growth is absent proceed.

(Step Q) Storage of "Formalinised Pilus/LPS Dialysate"

For longer term storage of the "formalinised LPS dialysate", place it at minus 20° C.

Day 14 or Later (Step R) Adjuvanting Stage One

Bring the "formalinised LPS dialysate" to 30° C. by placing it in a water bath. At the same time bring an equivalent volume of the adjuvant (MONTANIDE ISA 206) to 30° C. in a water bath.

Pour the adjuvant into a large beaker which has been sterilised by autoclaving (S13). Use the Ika laboratory mixer with the 3-blade paddle to stir the adjuvant at 200 RPM. Add the "formalinised LPS dialysate" gradually over 2 minutes. Increase the speed to 2,000 RPM and maintain for 10 minutes.

Store at 4° C. for 24 hours.

Day 15 or Later (Step S) Adjuvanting Stage Two

The day after Step L above, bring the "$1^{st}$ stage adjuvanted vaccine" to 30° C. in a water bath. Pour the warmed material into a large beaker which has been sterilised by autoclaving (S13). Use the Ika laboratory mixer with the 3-blade paddle to stir the material at 200 RPM for 2 minutes. Increase the speed to 2,000 RPM and maintain for 10 minutes. Store at 4° C. for 24 hours.

(Step T) Checking Quality of Emulsion

The day after Step M above, use a sterile Pasteur pipette to take a small aliquot of the "2nd stage adjuvanted vaccine". Fill a 250 mL beaker with approximately 200 mL of water. Place a drop of the aliquot onto the surface of the water. If the drop partially dilutes itself, giving a milky appearance to the water then it is water-in-oil-in-water and is acceptable. Store at 4° C. for 24 hours.

Day 16 or Later (Step U) Filling

Working in the biological safety cabinet, use a funnel and measuring container which have been sterilised by autoclaving to measure out the appropriate volume of the vaccine. For 250 mL pillow packs this is 253-255 mL Pour this material into pillow packs which have been sterilised by gamma radiation. Rubber stoppers and metal caps that have been sterilised by autoclaving are then used to close the top of each pillow pack. This process is then repeated until the appropriate number of pillow packs for the batch have been filled.

(Step V) Retention Sampling

Procure a retention sample.

(Step W) QC Sampling for Sterility Testing and Free Formalin Level Testing

Using the material left over at the end of the filling run, fill a 20 ml sample into a MacCartney bottle which has been sterilised by autoclaving. Use the same funnel and measuring container which were used to fill the rest of the run. Use this sample to perform sterility testing and free formalin level testing.

(Step X) Labelling

Label each batch.

Store in refrigerator.

(Step Y) First Sterility Check

Four days after filling, carry out the first check on the "sterility test tubes" and "sterility test plates" as described in Testing for Sterility.

(Step Z) Second Sterility Check

Seven days after filling, carry out the second check on the "sterility test tubes" and "sterility test plates" as described in Testing for Sterility.

(Step AA) Third Sterility Check

Eleven days after filling, carry out the third check on the "sterility test tubes" as described in Testing for Sterility.

(Step AB) Fourth Sterility Check

Fourteen days after filling, carry out the fourth check on the "sterility test tubes" as described in Testing for Sterility.

(Step AC) Product Use

The batch is acceptable for use if it satisfies the following specifications:

Physical appearance: a milky creamy liquid in a plastic pillow pack labelled with the approved format label including the name "Anadis E. coli Vaccine".

Purity: presence of a pure growth of E. coli on all purity test plates for each strain at the time of both first and second purity checks.

Sterility: absence of any indication of growth on plates or in tubes at the time of the sterility check and initial formal sterility test, or absence of any sign of growth during retesting as described in Testing For Sterility.

Potency: Greater than or equal to 1.0 mg of protein per mL of finished product.

Free Formalin Level: level in the QC sample is no greater than 0.002% w/v.

Emulsion quality: a drop of the emulsified vaccine placed on water partially dilutes itself, giving to the water a milky appearance.

Example 2

Preparation of Hyperimmune Colostrum

The vaccine prepared according to Example 1 was used for the preparation of hyperimmune colostrum as follows.

Cows are immunised, by a registered veterinarian, with a 2 ml injection of an emulsion of the vaccine in adjuvant into the muscle tissue on the side of the neck. Up to 5 injections are given at 2 weekly intervals during months 6 to 8.5 of gestation, ceasing 1 month before parturition. Test bleeds are taken from a selection of the immunised cows and assayed to determine the level of specific antibodies. Results of these assays are used determine if a satisfactory titre has been achieved.

To limit the possibility of self-inoculation, immunisations are only made by a registered veterinarian, with assistance from experienced cattle handling personnel. During immunisation, cows are suitably restrained eg. in a race, a crush or in a rotary milking carousel, to give clear access to the neck muscle. The injection site is clipped and disinfected before immunisation and subsequent injections are given on alternate sites in the same animal.

The method of manufacture after collection of the raw hyperimmune colostrum from the first milking is described below.

Example 3

Vaccine Preparation

This example describes the preparation of a vaccine according to a procedure typical of teachings of the prior art.

Bovine vaccines and the colostral antibodies against E. coli strain H10407, pilus antigens, and toxins were prepared according to the methods described below.

Preparation of Colostral Antibodies.

The antibodies were isolated from the colostrum of dairy cows immunized with enterotoxigenic E. coli strain H10407 and a selection of pilus antigens and heat-labile enterotoxin (LT). The cows under veterinary supervision and were housed in an experimental dairy farm. See J. Husu et al (1993).

Vaccine Preparation.

Bacterial antigens for the production of the vaccines were prepared from the enterotoxigenic E. coli strain H10407 (078: H11 CFA/I$^+$ ST$^+$ LT$^+$). Three antigens were purified from this strain:

(i) formalin-inactivated suspension of whole cells ($10^9$ bacteria per ml);

(ii) heat-labile enterotoxin (2 mg/ml)

(iii) CFA/I (2 mg/ml)

Vaccines were made by emulsifying an equal volume of each antigen with the same volume of Freund's incomplete adjuvant.

In addition to the above antigens, a commercial oil adjuvant vaccine containing purified pilus antigens from E. coli K88ac, K99 and 987P (E. coli Vaccine; Commonwealth Serum Laboratories Ltd.) was used.

Processing of Colostrums and Isolation of Whey Immunoglobulins.

Colostrum milk was collected from immunized cows during the first weeks of lactation. The milk was collected into individual containers and kept frozen until processing. Briefly, the milk fat was removed by centrifugation and skim milk was pasteurized at 56° C. for 30 minutes and then coagulated by renetting. After removal of milk curd containing casein, whey was centrifuged and the fine precipitate discarded. An equal volume of saturated ammonium sulphate solution was slowly added to the whey with continuous missing. After centrifugation, the resulting precipitate was saved and the supernatant containing lactose and salts was discarded.

The precipitate was dissolved in 0.32 M NaCl in 30% of original volume. This solution was extensively dialyzed against 5 volumes of saline using Amicon apparatus with the spiral membrane SIY 30 cartridge.

The antibody solution was concentrated to 10% solids, snap frozen, and freeze-dried. Finally, the freeze-dried antibody powder was sterilized by γ irradiation (25 KGrays). See Hilpert (1984), Antibodies—A laboratory Manual (1988) and Cravioto et al (1982).

Example 4

Determination of Cell Wall Separated O Antigens

This example provides a method for generating $10^6$ cfu/ml Gram negative bacteria, for removing O antigens from these bacteria and for determining the quantity of O antigens derived from the cell wall of these bacteria. The methods of this example enable the calculation of an "LPS-bacterial equivalent"—this is the amount of bacteria that will contain a given quantity of LPS. In the example below, 3 mg per ml of LPS is equivalent to $10^6$ cfu/ml of ETEC Gram negative bacteria.
Reagents
Phosphate Buffered Saline (PBS)
SDS-PAGE lysis buffer (20 ml) prepared as follows:

|  |  | [FINAL] |
|---|---|---|
| 2M Tris-HCl pH 6.8 | 10.0 ml | (1M) |
| dH$_2$O | 2.4 ml |  |
| 10% SDS | 4.0 ml | (2%) |
| glycerol | 2.0 ml | (10%) |
| 0.05% bromophenol blue | 0.8 ml | (0.002%) |
| Add 40 µl 2-mercaptoethanol per 960 µl buffer just before use (4%) | | |

Procedure
1. Bacterial strains are grown overnight at 37° C. on Nutrient Agar (NA) plates.
2. The following day bacteria are harvested into PBS and made up to a 0.5 McFarlane equivalent ($1 \times 10^8$ CFU/ml).
3. The bacterial suspension is then diluted 100 fold in PBS to give $1 \times 10^6$ CFU/ml.
4. This preparation is dispensed into 1 ml aliquots in sterile eppendorf tubes and centrifuged at 13000 rpm for three minutes to pellet the bacteria.
5. After centrifugation the supernatant is discarded and the pellet is resuspended in 50 µl of SDS-PAGE lysis buffer.
6. The samples are then boiled for ten minutes, cooled on ice briefly and pulsed in the centrifuge to collect condensation.
7. 2.5 µl of proteinase K (20 mg/ml) is added to each tube and incubated in a water bath at 60° C. for one hour.
8. After incubation an equal volume of phenol is added to each tube, vortexed and further incubated in a water bath at 65° C. for 15 minutes, vortexing every five minutes.
9. The sample is then centrifuged for ten minutes at 4° C. and the aqueous phase is recovered to a fresh tube for quantification of LPS.

Quantification of LPS
The Chromogenic *Limulus Amebocyte* Lysate (LAL) test is a quantitative test for Gram negative bacterial endotoxin. A sample is mixed with the LAL supplied in the kit and incubated at 37° C. for ten minutes. A substrate solution is then mixed with the LAL sample and incubated at 37° C. for a further six minutes. The reaction is stopped with 10% SDS. If endotoxin is present in the sample a yellow colour will develop measured at an absorbance of 405 nm. The amount of endotoxin in the sample is measured with the use of an endotoxin standard curve.
1. Phenol extracted LPS sample is diluted to 1 ml in LAL reagent water, and further dilutions prepared for assay in the LAL assay (1/10, 1/50, 1/250, 1/1250)
2. Endotoxin standard dilutions are prepared for standard curve (3 µg/ml-0.02 µg/ml) by making two fold serial dilutions in LAL reagent water.
3. Method for 96 well tray:

|  | Sample | Blank |
|---|---|---|
| Test sample or endotoxin standard | 50 µl | — |
| LAL reagent water | — | 50 µl |
| LAL | 50 µl | 50 µl |
| Mix and incubate at 37° C. for ten minutes | | |
| Chomogenic substrate | 100 µl | 100 µl |
| Mix and incubate at 37° C. for a further six minutes | | |
| Stop buffer (10% SDS) | 50 µl | 50 µl |

Read OD 405 nm on ELISA plate reader.
4. The OD measurements of the standard curve are then graphed (OD vs endotoxin concentration).
5. The unknown sample concentrations are then calculated by reading the OD off the standard curve and calculating the amount of endotoxin present.

Example 5

Treatment of Humans Using Hyperimmune Colostrum Extract

Protection from diarrhoea caused by enterotoxigenic *Escherichia coli* (ETEC H01047) by oral treatment with a tablet preparation of bovine colostrum extract sourced from cattle vaccinated against bacterial antigens and toxins.

Tablets were manufactured by Anadis Limited from the colostrum of dairy cattle immunised against multiple bacterial antigens and toxins. Two double blind control trials involved a total of 90 healthy volunteers and tested the protection given by forms of the tablet (and placebo) against a challenge dose of $1-2 \times 10^9$ *E. coli* O78.

The first study, with 30 participants, evaluated the effect of tablets containing 400 mg of colostrum extract taken with sodium bicarbonate buffer. There was 93.4% protection in the treatment group when compared to the placebo group of 26.7%. The second study tested tablets containing 400 mg colostrum extract given with buffer (85.7% protection) or without buffer (80% protection) and 200 mg colostrum extract given without the buffering drink (64.3% protection)—compared to the placebo group of 14.3%.

The active tablet formulations were significantly ($p<0.001$) better than the placebo treatments at protecting the volunteers from clinical signs of diarrhoea after challenge with pathogenic doses of enterotoxigenic *E. coli*. The studies suggest this tablet formulation of bovine colostrum extract containing antibodies against multiple enterotoxigenic bacteria and toxins has the potential to prevent clinical diarrhoea associated with these bacteria. The difference between buffered and unbuffered treatments was not statistically significant.

Example 6

Treatment of Humans Using Hyperimmune Colostrum

This example describes protection in human trial using a colostrum tablet made from hyperimmune colostrum induced by the vaccine described in Example 3.

Twenty two healthy adult volunteers were recruited and enrolled for a double blind challenge trial. Half were given *E. coli* specific bovine immunoglobulin tablets with bicarbonate solution or Skim milk placebo tablets with bicarbonate solution. The volunteers took their allotted treatment three times a day for 7 days. On the seventh day a challenge of $1 \times 10^9$ *E. coli* strain H010407 (ETEC O78) was given as a drink to all participants. The participants were then observed for signs of ETEC induced gastrointestinal disease.

Attack rate for diarrhoea in the groups was: 4/11 in the product group, 7/11 in the placebo group (p=0.2). The treatment (hyperimmune colostrum tablet) provided 44% protective efficacy against diarrhoea caused by ETEC H010407 when compared to the placebo group.

Example 7

Procedure of Antibody Titre Determination

This example describes an Elisa assay in which whole *E. coli* cells are coated on the microtitre plate. The assay is an antibody titre assay, and colour development is catalysed by goat anti-bovine IgG-peroxidase conjugate.

0.5 micrograms of heat-killed *E. coli* cells in 100 µl carbonate-bicarbonate coating buffer was dispensed into each well of a 96-well Maxisorp Immuno-plate (Nunc, Roskilde, Denmark), and left at 4° C. overnight. Plates were washed 6 times in PBS-0.05% TWEEN (polyoxyethylene (2) sorbitan monolaurate ($C_{58}H_{114}O_{26}$)) buffer, comprising 137 mM NaCl, 1.5 mM $KH_2PO_4$, 8 mM $Na_2HPO_4$, pH 7.4. 100 µl of each test serum or colostrum, diluted in PBS-TWEEN (polyoxyethylene (2) sorbitan monolaurate ($C_{58}H_{114}O_{26}$)) containing 12 mg/ml casein, were added to each well and incubated at 37° C. for 2 h. Plates were washed 6 times in PBS-TWEEN (polyoxyethylene (2) sorbitan monolaurate ($C_{58}H_{114}O_{26}$)) buffer, after which 100 µl goat anti-bovine IgG-peroxidase conjugate (Southern Biotacnology Associates, Inc., Birmingham, Ala., USA), diluted 1:4000 in PBS-TWEEN (polyoxyethylene (2) sorbitan monolaurate ($C_{58}H_{114}O_{26}$))-casein, were added to each well. Plates were incubated for 1 h at 37° C. and washed 6 times. 100 µl peroxidase substrate (Kirkegaard and Perry Lab. Inc., Gaithersburg, Md., USA) were added to each well and left at room temperature until colour developed. The reaction was stopped by the addition of 2 M sulphuric acid and the plates were read in a Diagnostics Pasteur LP400 plate reader (Sanofi, Mamesla-Coquette, France) at 450 mm. Results were expressed as the mean net O.D. (after subtraction of the blank reaction) of duplicate wells assayed on at least two separate occasions.

Example 8

Alternative Immunisation Protocol

Serum antibodies were produced using an antigen prepared according to Example 1. Cow immunisation was as described in example 2 except that three injections were given at 2-weekly intervals. Two weeks after the last of these injections, a blood sample was taken for antibody titre determination.

Example 9

Production of Serum Antibodies Using a Whole Cell Antigen

For the purposes of comparing the immunological response of separated cell wall antigens and whole cell antigens, serum antibodies were raised against whole cell antigens using the following procedure.

The whole cell antigen was made as follows: 100 ml of Luria broth was inoculated with *E. coli* H 10407 and incubated at 37° C. overnight with shaking. The resultant culture was centrifuged to pellet the bacteria, which was resuspended in 100 ml of sterile PBS and heated at 100° C. for 2.5 hours. The protein concentration was measured using the Bio-Rad protein assay, and adjusted to 1 milligram/ml. Adjuvanting was as described in example 1. Cows were vaccinated using the method of Example 7 and blood samples were withdrawn as described in Example 7.

Example 10

Comparison of Whole Cell Vs Separated Cell Wall Antigens

Sera derived from group A (18 cows) as per example 7 were run in the Elisa assay described in example 7. Sera derived from group B (14 cows) as per example 9 were also run in the Elisa assay of example 6. The results were:

|  | Group A | Group B |
|---|---|---|
| EIA units (av) | 860 | 96 |
| EIA (range) | 300-1600 | 30-300 |

The titre of antibodies raised using the vaccine of this invention (group A) was significantly greater than the titre of antibodies raised using the whole-cell vaccine (group B). This result is surprising because the titre was determined using whole cells immobilised on the Elisa plate.

Example 11

Animal Safety

An investigation of 1200 dairy cows vaccinated according to the protocol of example 2 showed no significant welfare problems or site reactions or loss in production.

Example 12

The following assay is based on the use of antibodies raised in the colostrum of cows to carry out an immunoblot analysis of colonisation factor. The antibodies are made according to the method of this invention, with the proviso that CFA (pilus) antigens are incorporated in the vaccine.

Buffers & Reagents

10× Tris/Glycine/SDS electrophoresis buffer:

| Tris | 15 g |
|---|---|
| Glycine | 72 g |
| SDS | 5 g |

Make up to 1 liter with dH$_2$O. Dilute 1/10 to make "working solution".

Transfer buffer (100 ml):

| Tris | 0.56 g |
|---|---|
| Glycine | 0.30 g |
| dH$_2$O | 80 ml |
| Methanol | 20 ml |
| 10% SDS | 360 μl |

Combine reagents in the above order and let cool before use.

3× Laemmli buffer (8 ml):

| dH$_2$O | 0.8 ml |
|---|---|
| 0.5M Tris-HCl pH 6.8 | 3.0 ml |
| Glycerol | 2.4 ml |
| SDS | 0.48 g |
| 2-β-Mercaptoethanol* | 1.2 ml |
| 0.05% (w/v) Bromophenol Blue | 0.6 ml |

*Add just before use.

Combine 1 volume Laemmli buffer with 2 vols sample.

Crude colonisation factor preparations

Spread enterotoxigenic *E. coli* (ETEC) strains on duplicate CFA plates and grow overnight at 37° C. (CF production) and room temperature (CF production suppressed). Scrape half a plate of cells into 1 ml PBS and pipette up and down to resuspend. Vortex briefly.

Incubate cell suspensions in a 60° C. waterbath for 30 mins to release colonisation factors. Pellet cells by centrifugation (14,000 rpm/20 mins) and recover supernatants to fresh tubes.

The crude preparation should contain both colonisation factor and LPS where expressed by the strains used.

SDS-PAGE

Pour 15% SDS-polyacrylamide gels with 4% stacking gel as follows:

| | 15% Separating (4 gels) | 4% Stacking (4 gels) |
|---|---|---|
| dH$_2$0 | 7.2 ml | 6.4 ml |
| 1M Tris pH 8.8 | 5 ml | NA |
| 0.5M Tris pH 6.8 | NA | 2.5 ml |
| ACCUGEL (40%) (a solution of 40% (w/v) acrylamide:bisacrylamide (29:1)) | 7.5 ml | 1 ml |
| 10% SDS | 200 μl | 100 μl |
| 10% APS | 100 μl | 50 μl |
| TEMED | 10 μl | 10 μl |
| Total vol | 20 ml | 10 ml |

Combine 2 vols each crude CF preparation and 1 vol 3× Laemmli buffer to give sufficient final volume ~25 μl per well required, (i.e. if loading each sample on duplicate gels combine 40 l CF and 20 l LB). Boil for 5 mins, cool on ice a spin briefly to collect condensation.

Load 20 μl of each sample per well and run gels for 30 mins at 100V (through stacking gel) and 1.5 hours at 150V (dye front will run off end).

Transfer proteins onto nitrocellulose using Trans-Blot apparatus (0.08 A max per mini gel, 30 mins) and block membranes overnight at 4° C. in PBS+0.1% TWEEN20 (polyoxyethylene (2) sorbitan monolaurate ($C_{58}H_{114}O_{26}$)) (PBS-T)+10% skim milk powder (SMP).

Immunoblot

Rinse blots with PBS-T (5 mins shaking)

Incubate blots with colostrum from cows hyperimmunised with a vaccine comprising CFA antigens (100 mg/ml in PBS) diluted 1/200 in PBS-T+5% SMP for 2 hours with gentle shaking.

Rinse blots and wash with PBS-T for 1×15 mins and 2×5 mins.

Incubate blots with goat anti-bovine IgG-HRPO (1/20,000) in PBS-T+5% SMP for 1 hour with gentle shaking.

Wash as above, drain excess PBS-T and place damp blots on an overhead sheet. Prepare ECL reagent, drop 1 ml on each gel and leave for 1 minute. Place another overhead sheet on top of blots and blot excess ECL reagent ensuring the top where the film will be placed is dry.

Expose the blots to X-ray film for the required amount of time (generally 3 mins initially and then work up or down from there).

Finally, it is understood that various other modifications and/or alterations may be made without departing from the spirit of the present invention as outlined herein.

REFERENCES

Hitchcock, P. J. and Brown, T. M (1983). Morphological heterogeneity among *Salmonella* lipopolysaccharide chemotypes in silver-stained polyacrylamide gels. Journal of Bacteriology, 154:269-277.

J. Husu et al. (1993) Production of hyperimmune bovine colostrums against *Campylobacter jejuni*. J Appl Bacteriol 74:564-569

H. Hilpert. (1984) Human Milk Banking, ed. A. F. Williams and J. D. Baum, Vevey/Raven Press, New York.

Antibodies—A Laboratory Manual, 1988, ed. By E. Harlow and D. Lane, Cold Spring Harbour Laboratory Press, p. 298-300.

A. Cravioto et al. (1982) Hemagglutination activity and colonization factor antigens I and II in enterotoxigenic and nontoxigenic strains of *Escherichia coli* isolated from humans. Infect Immun 36: 189-197.

J. Lyngby et al. (2002) Biologicals March: 30(1):7-13. Quantification of lipopolysaccharides . . . .

S. Y Li et al (2004) Analytical Biochemistry March 1: 326 (1): 1-12. Comparison of high-performance liquid chromatography and fluorophore-assisted carbohydrate electrophoresis methods for analysing peptidoglycan composition of *Escherichia coli*

Endotoxins in Health and Disease, eds H. Brade, S Opal, S Vogel, D Morrison; Marcel Dekker Inc 1999 Chapter 12 and other Chapters.

The invention claimed is:

1. A composition for use in the treatment or prophylaxis of enteric disease caused by Gram negative bacteria in a human individual, the composition comprising hyperimmune material prepared by immunizing an animal with a vaccine comprising O group serotype antigen, wherein said O antigen is prepared by separation from bacterial cell walls or wall fragments, wherein the O antigen is prepared by subjecting the intact cell walls of gram negative bacteria to shear and separating the O antigen from cell walls of the gram negative bacteria.

2. The composition according to claim 1 wherein the Gram negative bacteria are selected from the group consisting of *Helicobacter*, *Vibrio*, and *Enterobacteriaceae*.

3. The composition according to claim 2 wherein the Gram negative bacteria are *E. coli*.

4. The composition according to claim 3 wherein the *E. coli* are Enterotoxigenic *E. coli* (ETEC), Enterohemorrhagic *E. coli* (EHEC), or Enteropathogenic *E. coli* (EPEC).

5. The composition according to claim 1 wherein at least 20% of the O group serotype antigen is dissociated from bacterial cell walls or cell wall fragments.

6. The composition according to claim 1 wherein at least 40% of the O group serotype antigen is dissociated from bacterial cell walls or cell wall fragments.

7. The composition according to claim 1 wherein at least 80% of the O group serotype antigen is dissociated from bacterial cell walls or cell wall fragments.

8. The composition according to claim 1 wherein the animal is an ungulate animal.

9. A method of treatment or prophylaxis of enteric disease caused by Gram negative bacteria, said method comprising:
administering a composition to a human individual, wherein the composition comprises hyperimmune material prepared by immunizing an animal with a vaccine comprising O group serotype antigen, wherein said O antigen is prepared by separation from bacterial cell walls or wall fragments by subjecting the intact cell walls of gram negative bacteria to shear and separating the O antigen from cell walls of the gram negative bacteria.

10. A method of treatment or prophylaxis of enteric disease caused by Gram negative bacteria, said method comprising:
administering hyperimmune material raised against a vaccine to a human individual, wherein the vaccine comprises O group serotype antigens, wherein at least some of said antigens being separated from bacterial cell walls or wall fragments by subjecting the intact cell walls of gram negative bacteria to shear and separating the O antigen from cell walls of the gram negative bacteria.

11. The method according to claim 9 wherein the animal is an ungulate animal.

* * * * *